United States Patent
Blanz et al.

(10) Patent No.: US 7,034,529 B2
(45) Date of Patent: Apr. 25, 2006

(54) PHASE-ALTERNATED CARR-PURCELL NMR ECHO SEQUENCE

(75) Inventors: Martin Blanz, Celle (DE); Thomas Kruspe, Celle (DE)

(73) Assignee: Baker Hughes Incorporated, Houston, TX (US)

( * ) Notice: Subject to any disclaimer, the term of this patent is extended or adjusted under 35 U.S.C. 154(b) by 86 days.

(21) Appl. No.: 10/865,412

(22) Filed: Jun. 10, 2004

(65) Prior Publication Data

US 2005/0275401 A1    Dec. 15, 2005

(51) Int. Cl.
*G01V 3/00* (2006.01)
(52) U.S. Cl. ...................................... 324/303
(58) Field of Classification Search ............... 324/303, 324/307, 318
See application file for complete search history.

(56) References Cited

U.S. PATENT DOCUMENTS

| | | | |
|---|---|---|---|
| 6,204,663 B1 | 3/2001 | Prammer | 324/303 |
| 6,466,013 B1 | 10/2002 | Hawkes et al. | 324/303 |
| 6,522,138 B1 | 2/2003 | Heaton | 324/303 |
| 6,525,534 B1 | 2/2003 | Akkurt et al. | 324/303 |
| 6,570,381 B1 * | 5/2003 | Speier et al. | 324/303 |
| 6,624,629 B1 | 9/2003 | Speier et al. | 324/303 |
| 6,897,651 B1 * | 5/2005 | Reiderman et al. | 324/303 |
| 6,956,370 B1 * | 10/2005 | Heidler | 324/303 |
| 2003/0210043 A1 | 11/2003 | Freedman | 324/303 |
| 2004/0008027 A1 | 1/2004 | Prammer | 324/303 |
| 2004/0066192 A1 | 4/2004 | Heidler | 324/303 |

OTHER PUBLICATIONS

Eiichi Fukushima et al.; *Experimental Pulse NMR, a Nuts and Bolts Approach*, Addison-Wesley Publishing Company, Inc., Advanced Book Program, Jan. 1988, pp. 24-35.
C.P. Slichter; *Principles of Magnetic Resonance*, Third Enlarged and Updated Edition, pp. 366-371.

* cited by examiner

*Primary Examiner*—Louis Arana
(74) *Attorney, Agent, or Firm*—Madan, Mossman & Sriram, P.C.

(57) ABSTRACT

A phase alternated Carr Purcell (PACP) sequence is effective in removing DC offset from spin echo signals in earth formations. Modifications of PACP sequences, possibly in combination with other pulse sequences, can remove both DC offset and ringing. Such sequences may be used where the ringing is non-repeatable.

25 Claims, 7 Drawing Sheets

PHASE-ALTERNATED CARR-PURCELL NMR ECHO SEQUENCE

BACKGROUND OF THE INVENTION

1. Field of the Invention

The present invention relates to the field of Nuclear Magnetic Resonance logging of geological formations. Specifically, the invention is a method of phase-alternated RF induction of nuclear spins.

2. Description of the Related Art

A variety of techniques are utilized in determining the presence and estimation of quantities of hydrocarbons (oil and gas) in earth formations. These methods are designed to determine formation parameters, including among other things, the resistivity, porosity and permeability of the rock formation surrounding the wellbore drilled for recovering the hydrocarbons. Typically, the tools designed to provide the desired information are used to log the wellbore. Much of the logging is done after the well bores have been drilled. More recently, wellbores have been logged while drilling, which is referred to as measurement-while-drilling (MWD) or logging-while-drilling (LWD).

One recently evolving technique involves utilizing Nuclear Magnetic Resonance (NMR) logging tools and methods for determining, among other things, porosity, hydrocarbon saturation and permeability of the rock formations. The NMR logging tools are utilized to excite the nuclei of fluids in the geological formations surrounding the wellbore so that certain parameters such as spin density, longitudinal relaxation time (generally referred to in the art as $T_1$) and transverse relaxation time (generally referred to as $T_2$) of the geological formations can be measured. From such measurements, porosity, permeability and hydrocarbon saturation are determined, which provides valuable information about the make-up of the geological formations and the amount of extractable hydrocarbons.

The NMR tools generate a uniform or near uniform static magnetic field in a region of interest surrounding the wellbore. NMR is based on the fact that the nuclei of many elements have angular momentum (spin) and a magnetic moment. The nuclei have a characteristic Larmor resonant frequency related to the magnitude of the magnetic field in their locality. Over time the nuclear spins align themselves along an externally applied magnetic field. This equilibrium situation can be disturbed by a pulse of an oscillating magnetic field, which tips the spins with resonant frequency within the bandwidth of the oscillating magnetic field away from the static field direction. The angle θ through which the spins exactly on resonance are tipped is given by the equation:

$$\theta = \gamma B_1 t_p / 2 \quad (1)$$

where γ is the gyromagnetic ratio, $B_1$ is the magnetic flux density amplitude of the sinusoidally oscillating field and $t_p$ is the duration of the RF pulse.

After tipping, the spins precess around the static field at a particular frequency known as the Larmor frequency $\omega_0$, given by $$\omega = \gamma B_0 \quad (2)$$

where $B_0$ is the static field intensity. At the same time, the spins return to the equilibrium direction (i.e., aligned with the static field) according to an exponential decay time known as the spin-lattice relaxation time or $T_1$. For hydrogen nuclei, $\gamma/2\pi = 4258$ Hz/Gauss, so that a static field of 235 Gauss would produce a precession frequency of 1 MHz. $T_1$ of fluid in pores is controlled totally by the molecular environment and is typically ten to one thousand milliseconds in rocks.

At the end of a θ=90° tipping pulse, spins on resonance are pointed in a common direction perpendicular to the static field, and they precess at the Larmor frequency. However, because of inhomogeneity in the static field due to the constraints on tool shape, imperfect instrumentation, or microscopic material heterogeneities, each nuclear spin precesses at a slightly different rate. Hence, after a time long compared to the precession period, but shorter than $T_1$, the spins will no longer be precessing in phase. This de-phasing occurs with a time constant that is commonly referred to as $T_2^*$ if it is predominantly due to the static field inhomogeneity of the apparatus, and as $T_2$ if it is due to properties of the material.

One method to create a series of spin echoes is due to Carr and Purcell. Discussed in Fukusima, E., and Roeder, B., "Experimental Pulse NMR: A Nuts and Bolts Approach", 1981, as well as Slichter, C. P., "Principles of Magnetic Resonance", 1990. The pulse sequence starts with a delay of several $T_1$ to allow spins to align themselves along an applied static magnetic field axis. Then a 90° tipping pulse is applied to rotate the spins into the transverse plane, where they precess with angular frequency determined by local magnetic field strength. The spin system loses coherence in accordance with time constant, $T_2^*$. After a short time ($t_{CP}$) a 180° tipping pulse is applied which continues to rotate the spins, inverting their position in the transverse plane. The spins continue to precess, but now their phases converge until they momentarily align a further time $t_{CP}$ after application of the 180° pulse. The realigned spins induce a voltage in a nearby receiving coil, indicating a spin echo. Another 180° pulse is applied after a further time $t_{CP}$, and the process is repeated many times, thereby forming a series of spin echoes with spacing 2 $t_{CP}$.

While the Carr-Purcell sequence would appear to provide a solution to eliminating apparatus induced inhomogeneities, it was found by Meiboom and Gill that if the duration of the 180° pulses in the Carr-Purcell sequence were even slightly erroneous so that focusing is incomplete, the transverse magnetization would steadily be rotated out of the transverse plane. As a result, substantial errors would enter the $T_2$ determination. Thus, Meiboom and Gill devised a modification to the Carr-Purcell pulse sequence such that after the spins are tipped by 90° and start to de-phase, the carrier of the 180° pulses is phase shifted by π/2 radians relative to the carrier of the 90° pulse. This phase change causes the spins to rotate about an axis perpendicular to both the static magnetic field axis and the axis of the tipping pulse. If the phase shift between tipping and refocusing pulses deviates slightly from π/2 then the rotation axis will not be perfectly orthogonal to the static and RF fields, but this has negligible effect. For an explanation, the reader is referred to a detailed account of spin-echo NMR techniques, such as in Fukushima and Roeder, "Experimental Pulse NMR: A Nuts and Bolts Approach". As a result any error that occurs during an even numbered pulse of the CPMG sequence is cancelled out by an opposing error in the odd numbered pulse. The CPMG sequence is therefore tolerant of imperfect spin tip angles. This is especially useful in a well logging tool which has inhomogeneous and imperfectly orthogonal static and pulse-oscillating (RF) magnetic fields.

A typical CPMG sequence is shown in FIG. 2. Excitation pulse 201 rotates the magnetic spins into the xy-plane. Refocusing pulses (202a, 202b, 202c, 202d, 202e . . . ) are applied following the excitation pulse, each of which induce a spin echo (203a, 203b, 203c, 203d, 203e . . . ). Although the illustration of FIG. 2 is limited to five refocusing pulses, in reality there can be hundreds or thousands of pulses and echoes. The time between the centers of two subsequent echoes is called inter-echo spacing TE. The curve linking the echo maxima is the echo decay curve 210. All refocusing pulses have the same phase. The phase of the excitation pulse is offset by either +90° or −90°. Some characteristics of the CPMG sequence are:

a) The excitation pulse tips the z-magnetization (aligned with the static magnetic field) into the xy-plane perpendicular to the z-axis.
b) The refocusing pulses rotate the magnetization by 180°.
c) If all pulses have the same amplitude, then refocusing pulses are twice the length of the excitation pulse.
d) All refocusing pulses have the same phase, but the excitation pulse phase is 90° different.

The last characteristic d) was the novelty when the CPMG was first published. This phase shift between excitation pulse and refocusing pulses causes a compensation of rephasing angle errors. With the phase shift the errors correct themselves with every second echo.

As noted above, the CPMG sequence tolerates imperfect spin tip angles. As an example, U.S. Pat. No. 6,466,013, to Hawkes et al. discusses a method, referred to as the Optimized Rephasing Pulse Sequence (ORPS), which optimizes the timings for inhomogeneous $B_0$ and $B_1$ fields to obtain maximum NMR signal or, alternatively, to save radio frequency power. A pulsed RF field is applied which tips the spins on resonance by the desired tip angle for maximum signal, typically 90° tipping pulse. A refocusing pulse having a spin tip angle substantially less than 180° is applied with carrier phase shifted by typically $\pi/2$ radians with respect to the 90° tipping pulse. Although the refocusing pulses result in spin tip angles less than 180° through the sensitive volume, their RF bandwidth is closer to that of the original 90° pulse. Hence more of the nuclei originally tipped by 90° are refocused, resulting in larger echoes than would be obtained with a conventional 90° refocusing pulse. ORPS is not a CPMG sequence. The timing and duration of RF pulses are altered from conventional CPMG to maximize signal and minimize RF power consumption. Nevertheless ORPS still possesses the characteristic d), i.e. the excitation pulse is phase shifted by 90° with respect to the refocusing pulses. An additional forced recovery pulse at the end of an echo train may be used to speed up the acquisition and/or provide a signal for canceling the ringing artifact.

The NMR echoes of an echo sequence like CPMG or ORPS contain, in addition to the true NMR signal, DC offset and ringing. Radio frequency pulses typically cause ringing (magneto-acoustic, electronic) after each pulse. This ringing can be larger than the NMR signal itself. It must be avoided or subtracted before further processing of the NMR data. DC offset of the NMR signals must also be determined and subtracted. We refer to the DC offset and ringing as non-NMR signals to distinguish them from NMR signals from nuclei in earth formations.

Subtraction methods for reducing ringing and offset are known in the prior art. The standard method for this is the use of a Phase Alternated Pair (PAP) of echo sequences.

In order to cancel the electronic offsets and antenna ringing, it is customary to combine two CPMG measurements of opposite phase. These pairwise-combined measurements are called phase-alternate-pair (PAP) echo trains and these constitute the datasets that are submitted to processing. U.S. Pat. No. 6,624,629, to Kleinberg et al., discusses a standard PAP method. In a PAP sequence, two CPMG or ORPS sequences are acquired. In one sequence, the excitation pulse rotates the nuclear spins by −90° with respect to the refocusing pulses, and in the other sequence, the excitation pulse rotates the nuclear spin by +90° with respect to the refocusing pulses. The inverted phase of the alternate excitation pulse causes a phase inversion of all the echoes. Meanwhile the effects of ringing due to the refocusing pulses are unaffected by the inversion of the excitation pulses. A typical PAP sequence is shown in FIG. 3. By subtracting the acquired echo data of the lower sequence of FIG. 3 from those of the upper sequence, the ringdowns of all refocusing pulses and the offsets are subtracted while the NMR echoes are added.

A condition for proper ringdown and offset subtraction of the PAP is that the ringdown and offset are repeatable, i.e. identical in both sequences that make up the PAP.

U.S. Pat. No. 6,522,138, to Heaton and U.S. Pat. No. 6,525,534, to Akkurt et al. discusses method of reducing ringing effects. Heaton '138 discusses retrieving corrected individual measurements from sequentially parwise-combined measurements. Such sequentially pairwise-combined measurements may include PAP NMR measurements from well logging. One of the methods comprises providing an initial estimate for a first one of the corrected individual measurement, deriving temporary estimates for other ones of the corrected individual measurements by subtracting the initial estimate from the first sequentially pairwise-combined measurements to produce an estimate for a second one of the corrected individual measurements, and repeating the subtraction from each of the next sequentially pairwise-combined measurements until temporary estimates for each of the corrected individual measurements are obtained, and correcting errors in the temporary estimates to generate error-corrected estimates by filtering an alternating error component associated with the initial estimate. Akkurt '534 discusses improving the vertical resolution of NMR logs based on data acquisition methods and signal processing techniques that need not apply PAPS. The method of Akkurt '534 is based on reducing the level of coherent non-formation signals, but providing estimates of these signals and removing the estimates from the underlying NMR pulse echo trains.

Alternate methods for improving resolution are discussed in the prior art. U.S. Patent Appl. No. 2004/0008027, of Prammer, discusses providing, in a geologic formation, at least one first plurality of phase alternated NMR pulses at a first frequency ($F_1$), and receiving at least one corresponding first signal in response. The method includes providing, not necessarily simultaneously, at least one second plurality of phase alternated NMR pulses at a second frequency ($F_2$), and receiving at least one corresponding second signal in response thereto. In an embodiment of Prammer a difference between the first and second frequencies is a function of one or more of an inter-echo spacing, a time delay between and excitation pulse and a data acquisition window, and a rate for generating echoes. The received first and second signals are combined to obtain a corrected NMR signal.

U.S. Pat. No. 6,624,629, to Speier et al., uses a controller adapted to cause the RF transmitter to transmit RF pulse sequences into a sample and for each different RF pulse sequence, vary an estimated pulse width for producing a predetermined flip angle by a different scaling facto to produce flip angles near the predetermined flip angle. The controller is adapted to receive spin echo signals in response to the transmission of the RF pulse sequences; determine a property of the sample in response to the spin echo signals; and use the spin echo signals to determine an optimal pulse width for producing the predetermine flip angle.

The technique of PAP depends on the repeatability of offset and ringing. Between the acquisition of the two echo sequences may be a remagnetization delay of up to 10 seconds. In reality, both offset and ringing may not be stable over such a long time. Yet another disadvantage of PAP is that a complete NMR measurement takes at least two echo sequences with a (long) remagnetization time between them. For fast NMR (wireline) logging this is a disadvantage because the aperture of the NMR measurement along the borehole axis is increased. Therefore there are quite a number of reasons to look for alternatives to PAP for subtracting offset and ringing from the NMR signal. The present invention fulfills those needs.

SUMMARY OF THE INVENTION

The present invention is a method of and apparatus for evaluating an earth formation. A nuclear magnetic resonance (NMR) device is conveyed within a borehole in the earth formation. A magnet on the NMR device produces a static magnetic field in a volume of the earth formation. The static magnetic field aligns nuclear spins in the formation. The earth formation is pulsed by at least one sequence of radio frequency (RF) pulses. The RF pulse sequence includes an excitation pulse with a tip angle substantially equal to 90° and a plurality of groups of refocusing pulses, each group including a phase-alternated pair of refocusing pulses, one pulse of said phase-alternated pair having a phase substantially equal to a phase of the excitation pulse. The pulsing may be done by an antenna assembly. Signals resulting from the application of the pulses are received. The resulting signals are processed to give corrected signals in which a non formation signal has been reduced. The processing may be done by a processor. In one embodiment of the invention, the signals are spin echo signals.

In one embodiment of the invention, the non-formation signal is a DC offset. In another embodiment of the invention, each group of refocusing pulses includes refocusing pulses that are phase shifted plus or minus 90° to a phase of the excitation pulse: this enables removal of ringing.

The refocusing pulses may have tip angles substantially equal to 180°. In another embodiment of the invention, the refocusing pulses have tip angles between 90° and 180°. The corrected signals may be processed using a processor to determine formation properties such as total porosity, effective porosity, BVI, BVM, and, $T_2$ distribution. The NMR apparatus may be part of a bottom hole assembly used for drilling a borehole or may be conveyed on a wireline.

BRIEF DESCRIPTION OF THE DRAWINGS

The present invention is best understood with reference to the accompanying figures in which like numerals refer to like elements and in which.

DETAILED DESCRIPTION OF THE INVENTION

Figure 1:
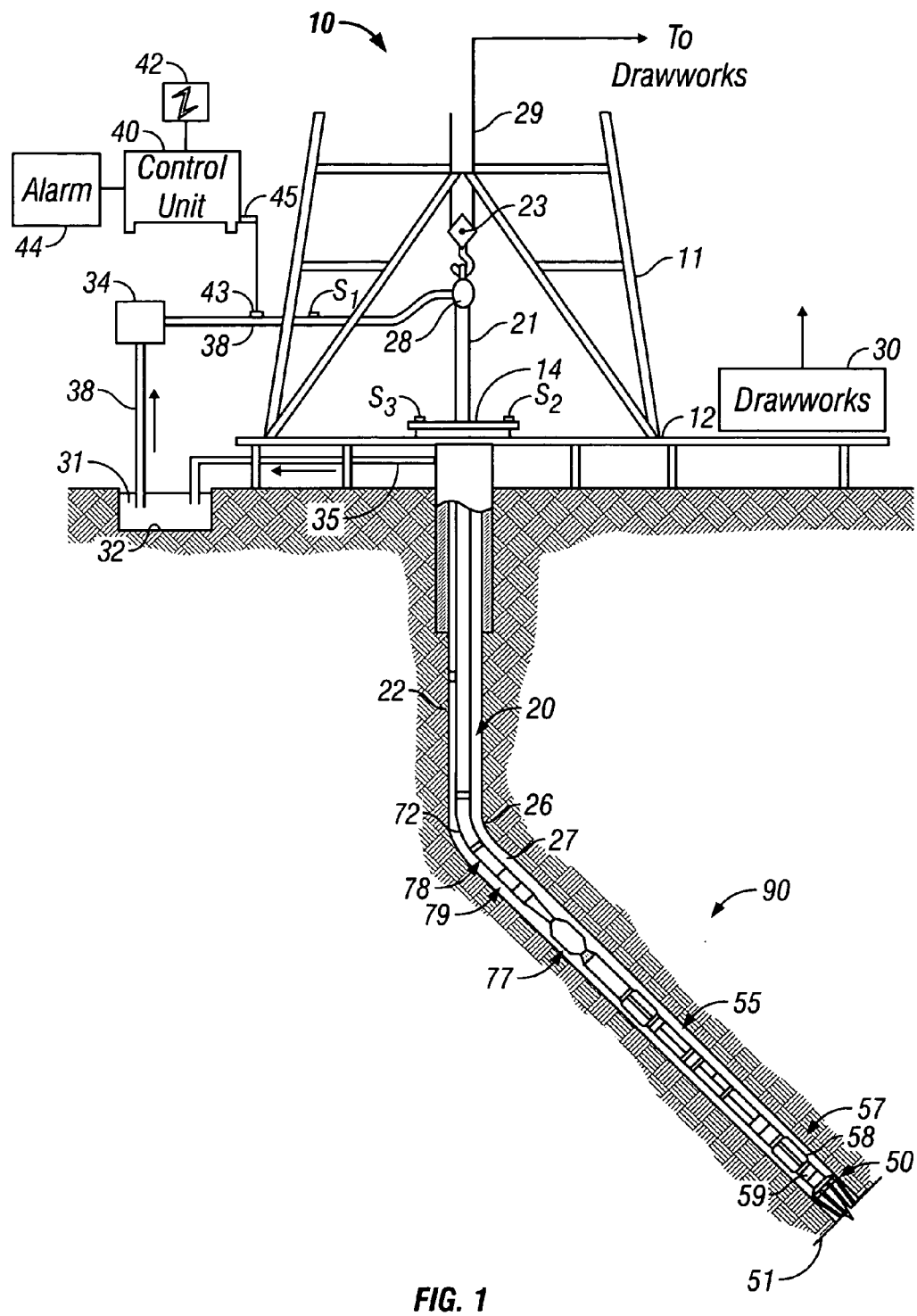
FIG. 1 (Prior Art) shows a measurement-while-drilling tool suitable for use with the present invention.
Figure 2:
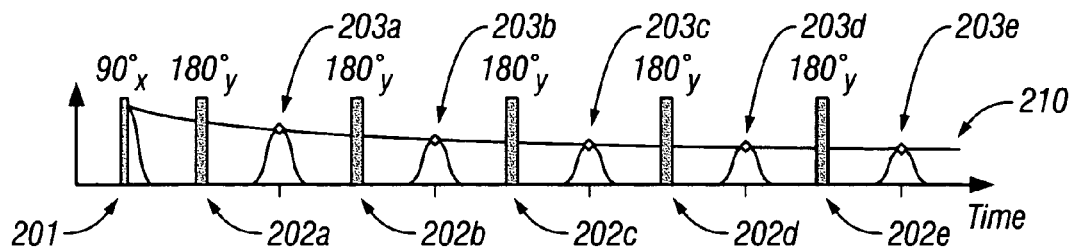
FIG. 2 (Prior Art) shows a typical CPMG sequence.
Figure 3:
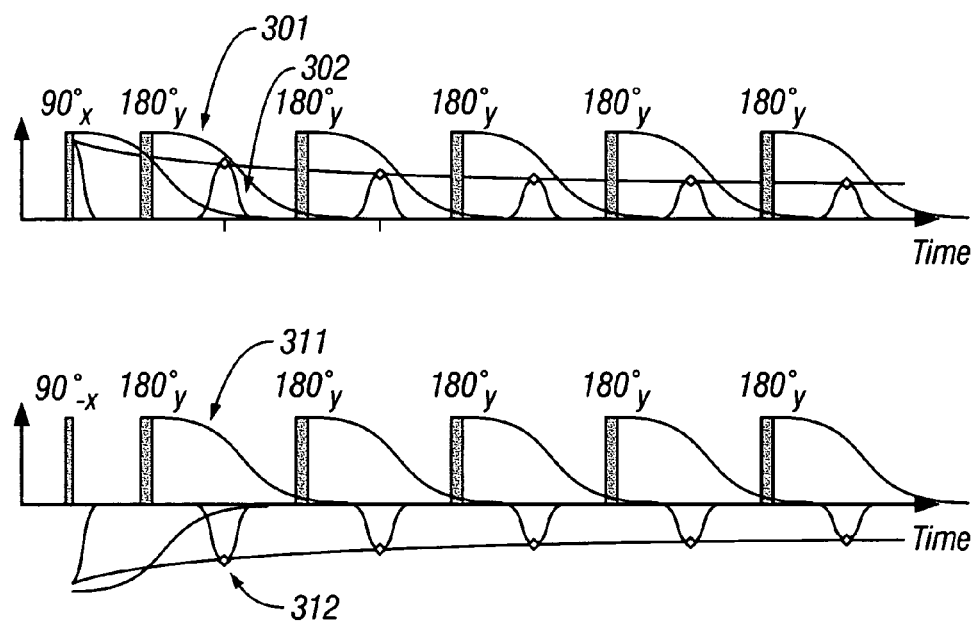
FIG. 3 (Prior Art) shows a phase-alternated pair sequence (PAPS)

FIG. 1 shows a schematic diagram of a drilling system 10 with a drillstring 20 carrying a drilling assembly 90 (also referred to as the bottom hole assembly, or "BHA") conveyed in a "wellbore" or "borehole" 26 for drilling the wellbore. The drilling system 10 includes a conventional derrick 11 erected on a floor 12 which supports a rotary table 14 that is rotated by a prime mover such as an electric motor (not shown) at a desired rotational speed. The drillstring 20 includes a tubing such as a drill pipe 22 or a coiled-tubing extending downward from the surface into the borehole 26. The drillstring 20 is pushed into the wellbore 26 when a drill pipe 22 is used as the tubing. For coiled-tubing applications, a tubing injector, such as an injector (not shown), however, is used to move the tubing from a source thereof, such as a reel (not shown), to the wellbore 26. The drill bit 50 attached to the end of the drillstring breaks up the geological formations when it is rotated to drill the borehole 26. If a drill pipe 22 is used, the drillstring 20 is coupled to a drawworks 30 via a Kelly joint 21, swivel 28, and line 29 through a pulley 23. During drilling operations, the drawworks 30 is operated to control the weight on bit, which is an important parameter that affects the rate of penetration. The operation of the drawworks is well known in the art and is thus not described in detail herein.

During drilling operations, a suitable drilling fluid 31 from a mud pit (source) 32 is circulated under pressure through a channel in the drillstring 20 by a mud pump 34. The drilling fluid passes from the mud pump 34 into the drillstring 20 via a desurger (not shown), fluid line 38 and Kelly joint 21. The drilling fluid 31 is discharged at the borehole bottom through an opening in the drill bit 50. The drilling fluid 31 circulates uphole through the annular space 27 between the drillstring 20 and the borehole 26 and returns to the mud pit 32 via a return line 35. The drilling fluid acts to lubricate the drill bit 50 and to carry borehole cutting or chips away from the drill bit 50. A sensor $S_1$ typically placed in the line 38 provides information about the fluid flow rate. A surface torque sensor $S_2$ and a sensor $S_3$ associated with the drillstring 20 respectively provide information about the torque and rotational speed of the drillstring. Additionally, a sensor (not shown) associated with line 29 is used to provide the hook load of the drillstring 20.

In one embodiment of the invention, the drill bit 50 is rotated by only rotating the drill pipe 22. In another embodiment of the invention, a downhole motor 55 (mud motor) is disposed in the drilling assembly 90 to rotate the drill bit 50 and the drill pipe 22 is rotated usually to supplement the rotational power, if required, and to effect changes in the drilling direction.

In an exemplary embodiment of FIG. 1, the mud motor 55 is coupled to the drill bit 50 via a drive shaft (not shown) disposed in a bearing assembly 57. The mud motor rotates the drill bit 50 when the drilling fluid 31 passes through the mud motor 55 under pressure. The bearing assembly 57 supports the radial and axial forces of the drill bit. A stabilizer 58 coupled to the bearing assembly 57 acts as a centralizer for the lowermost portion of the mud motor assembly.

In one embodiment of the invention, a drilling sensor module 59 is placed near the drill bit 50. The drilling sensor module contains sensors, circuitry and processing software and algorithms relating to the dynamic drilling parameters. Such parameters typically include bit bounce, stick-slip of the drilling assembly, backward rotation, torque, shocks, borehole and annulus pressure, acceleration measurements and other measurements of the drill bit condition. A suitable telemetry or communication sub 72 using, for example, two-way telemetry, is also provided as illustrated in the drilling assembly 90. The drilling sensor module processes the sensor information and transmits it to the surface control unit 40 via the telemetry system 72.

The communication sub 72, a power unit 78 and an MWD tool 79 are all connected in tandem with the drillstring 20. Flex subs, for example, are used in connecting the MWD tool 79 in the drilling assembly 90. Such subs and tools form the bottom hole drilling assembly 90 between the drillstring 20 and the drill bit 50. The drilling assembly 90 makes various measurements including the pulsed nuclear magnetic resonance measurements while the borehole 26 is being drilled. The communication sub 72 obtains the signals and measurements and transfers the signals, using two-way telemetry, for example, to be processed on the surface. Alternatively, the signals can be processed using a downhole processor in the drilling assembly 90.

The surface control unit or processor 40 also receives signals from other downhole sensors and devices and signals from sensors $S_1-S_3$ and other sensors used in the system 10 and processes such signals according to programmed instructions provided to the surface control unit 40. The surface control unit 40 displays desired drilling parameters and other information on a display/monitor 42 utilized by an operator to control the drilling operations. The surface control unit 40 typically includes a computer or a microprocessor-based processing system, memory for storing programs or models and data, a recorder for recording data, and other peripherals. The control unit 40 is typically adapted to activate alarms 44 when certain unsafe or undesirable operating conditions occur.

Figure 4:
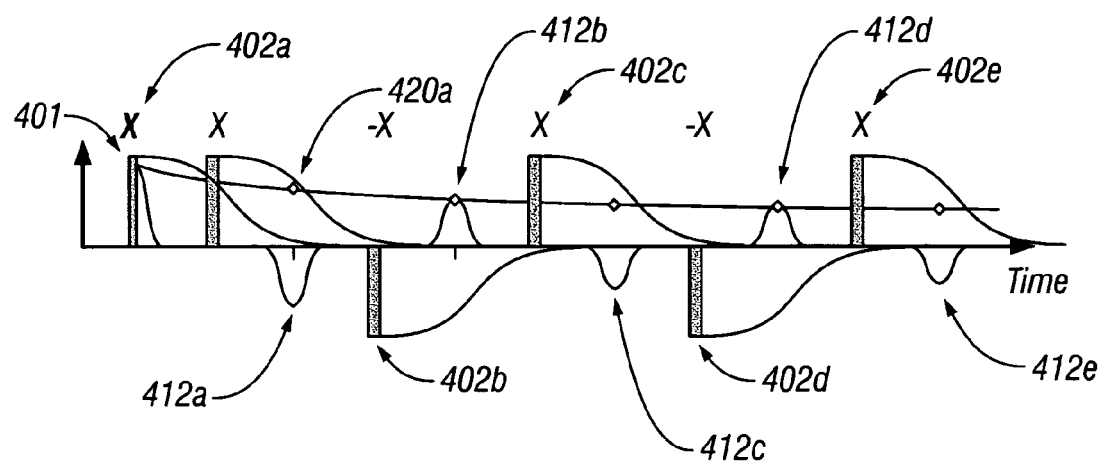
FIG. 4 shows an exemplary pulse sequence of the present invention.

FIG. 4 shows an exemplary pulse sequence of the present invention. This pulse sequence is a variation on the original CP pulse sequence. The echo sequence of FIG. 4 has been suggested, for example, in Fukushima and Slichter but without foreseeing their advantage in NMR logging in very inhomogeneous fields. Since we have not a name for this sequence in the literature, we refer to it herein as the Phase Alternated Carr Purcell (PACP) sequence.

A static magnetic field is introduced into a volume, the direction of the magnetic field defining a coordinate system wherein the +Z axis is substantially aligned along the static magnetic field in the volume and X and Y axes define a plane substantially perpendicular to said static magnetic field. For discussion purposes, the applied RF pulses rotate the nuclear spins along the X-axis.

The following is a concise notation for the pulse sequences used in the present document.

x (y)n denotes an x excitation pulse followed by n y pulses;

−x (y)n denotes a −x excitation pulse followed by n y pulses; and x (y y −y −y)n denotes an x excitation pulse followed by n repetitions of (y y −y −y) pulses. The latter may be called a CPMG derivative because the sequence uses a refocusing pulse phase shift of $\pm\pi/2$ with respect to the excitation pulse and not all refocusing pulses have the same phase.

The phase alternated Carr Purcell sequence is denoted by X (x −x)n or X (−x x)n. An excitation pulse 401 is applied so as to tilt the nuclear spins into the plane transverse to the static magnetic field. The rotation of the spins due to the excitation pulse occurs along the X-axis, so that nuclear spins are aligned along the Y-axis directly after the completion of the excitation pulse. The excitation pulse typically has a tipping angle of around 90°. The excitation pulse is followed after a time $t_{CP}$ with phase-alternated pairs of refocusing pulses. In the pulse sequence of FIG. 4, for example, refocusing pulses 402a, 402c, and 402e rotate the nuclear spins +180° around the X-axis, whereas refocusing pulses 402b and 402d rotate the nuclear spins −180° around the X-axis. Pulses 402a and 402b form a phase-alternate pulse pair, as do pulses 402c and 402d. Although the illustration of FIG. 4 shows only five echoes, the number of refocusing pulses is not limited in number by the present invention. Spin echoes (412a, 412b, 412c, 412d, 412e, . . . ) resulting from the phase-alternated refocusing pulses therefore experience a 180° phase shift from each other. It should be noted that the tipping angle of the refocusing pulses could by 180° (as with a CPMG sequence) or could be less than 180° (as with the ORPS sequence). While the spin echoes experience a 180° shift, the DC offset of the signal does not experience the same shift.

One advantage of the application of the pulse sequence of FIG. 4 is that the resultant spin echo signals can be used to remove DC offset without the use of a PAPS. For example, one can combine (subtract) successive spin echoes of the spin echo sequence. Such subtraction enables removal of the offset while co-adding NMR. An exemplary algorithm for signal-removal is:

Echo 2−echo 1=positive, offset-free echo at position midway between echo 1 and echo 2.

Echo 2−Echo 3=positive, offset-free echo at position midway between echo 2 and echo 3.

Echo 4−Echo 3=positive, offset-free echo at position midway between echo 3 and echo 4.

Echo 4−Echo 5=positive, offset-free echo at position midway between echo 4 and echo 5.

and so forth. PS In reference to FIG. 4, the above algorithm would be written as: echo 412b−echo 412a; echo 412b−echo 412c; echo 412d−echo 412c; echo 412d−echo 412e; and so forth. The removal of the DC offset is enabled by the spin echoes alternating in phase as the DC offset remains in phase.

Figure 6:
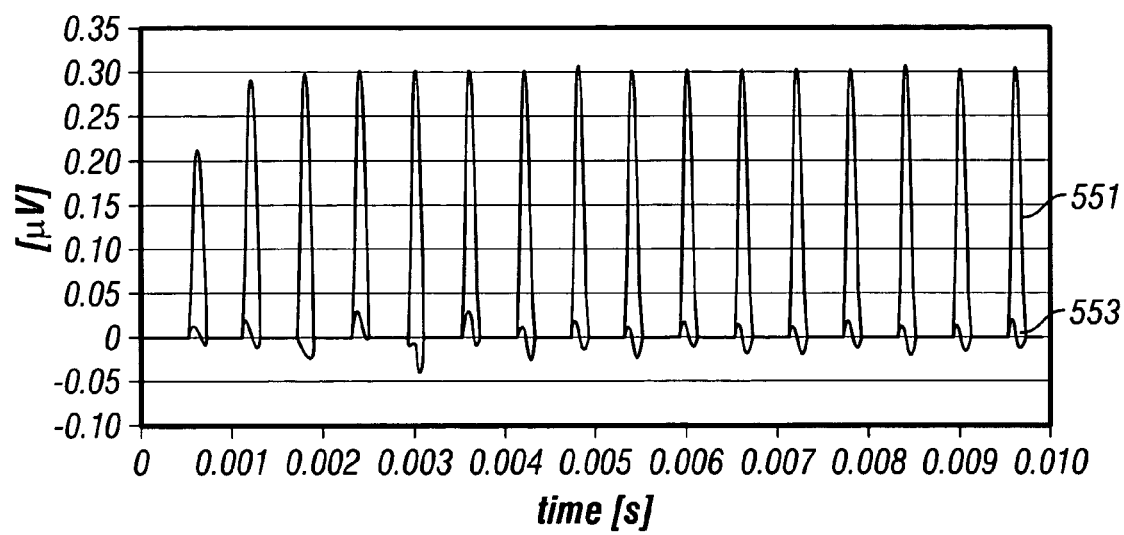
FIG. 6 shows a simulation of an ORPS sequence.
Figure 7:
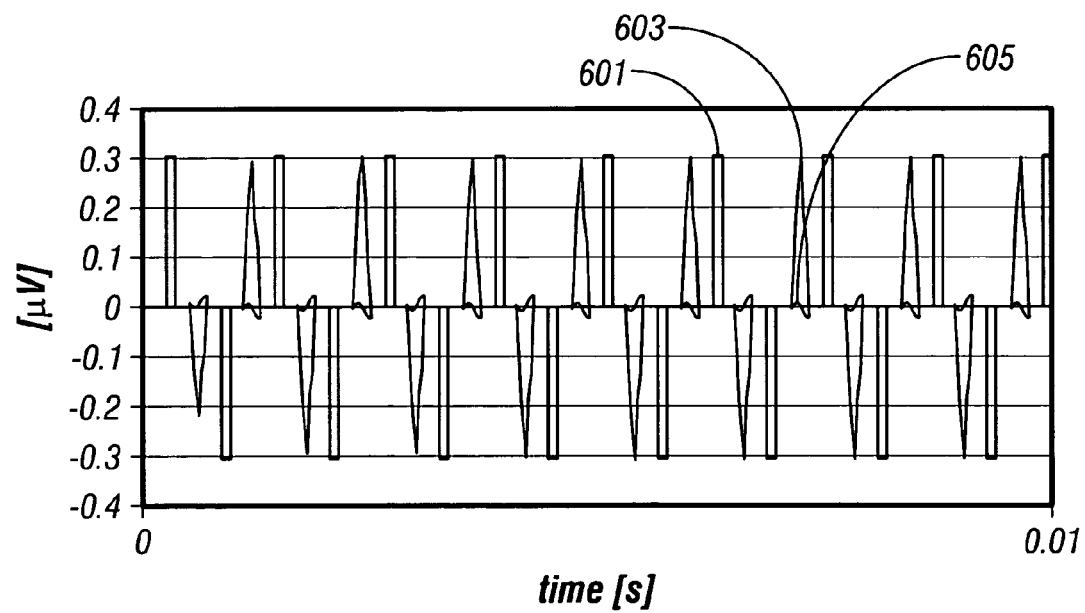
FIG. 7 shows a simulation of a PACP spin echo sequence.

FIG. 6 shows signals resulting from a simulation of an ORPS sequence. The echoes are each shown with in-phase 551 and quadrature components 553. In FIG. 7, a simulation of a spin echo sequence resulting from a PACP is shown. The pulses are shown by 601, the real component of the echoes by 603 and the quadrature component of the echoes by 605. As in CPMG and ORPS, the pulse errors of the PACP no longer accumulate but cancel. The PACP sequence works in inhomogeneous static and RF fields as effectively as the CPMG or ORPS sequence (depending on timing). Peak amplitudes of FIG. 7 are substantially equal to peak amplitudes of FIG. 6. The sequence of FIG. 7 also has the same sensitivity to motion as FIG. 6.

Provided ringing is negligible, the offset removal method discussed above avoids the need for a PAP. Therefore, an improved DC offset removal (where the offset varies with time) is achieved. As a result, the resolution along the borehole axis is enhanced.

PACP by itself does not enable removal of ringing as it does removal of DC 20 offset. This is because there is always the same phase relation between each refocusing pulse (and its resultant ringdown) and its corresponding spin echo within a pulse sequence. Said another way, the signs of the spin echo alternate from echo to echo but so do the signs of the refocusing pulses (and ringdowns). Therefore, there is no pairing of echoes in PACP that can be used to remove ringing while at the same time accumulating the NMR signal.

Figure 5:
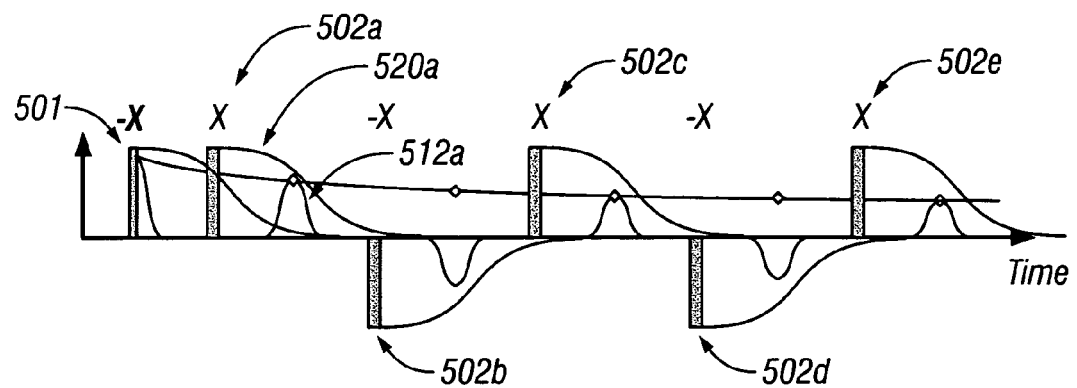
FIG. 5 shows a variation on the pulse sequence of the present invention.

A PAP combination of the PACP can be constructed for reducing ringing effects. Like the CPMG pulse sequence, the excitation pulse of the PACP enables two variations. A PAPS sequence can be constructed from the two PACP sequences for reducing ringing effects. FIG. 5 shows a second pulse sequence of the present invention. FIG. 5 is similar to FIG. 4 in that an excitation pulse 501 is applied followed by alternating refocusing pulses (502a, 502b, 502c, 502d, 502e . . . ). Whereas the excitation pulse 401 of FIG. 4 rotates the nuclear spins in the +90° direction around the X-axis, the excitation pulse 501 of FIG. 5 rotates the nuclear spins in the −90° direction around the X-axis. The refocusing pulses of FIG. 5 are in phase with the refocusing pulses of FIG. 4. As a result, the ringdown of the refocusing pulses is identical in both sequences (e.g. the phase of ringdown 420a is the same as the phase of ringdown 520a). However, the spin echoes of FIG. 5 are inverted in phase from the corresponding spin echoes of FIG. 4. Due to these phase relations between spin echoes and ringdowns in FIGS. 4 and 5, when subtracting the two variant spin echo sequences (i.e. the signals due to refocusing pulses 502a and 402a), the ringdowns (520a, 420a) are subtracted simultaneously with the addition of the spin echoes (512a, 412a).

An alternative PAPS can be constructed where both PACP sequences of the PAPS have the same excitation pulse phase but all the refocusing pulses have been phase-inverted in one sequence with respect to the other.

The pulse times and delay times of a pulse sequence of the present invention can be optimized according to methods discussed in Hawkes '013 and in Slichter.

We next address the issue of removing ringing using a variant of the PACP sequence in combination with CPMG or ORPS sequences. Eight such sequences are possible, claim 8 denoted by:

X (x −x y y)$_n$,
X (y y x −x)$_n$,
X (−x x y y)$_n$,
X (y y −x x)$_n$,
X (x −x −y −y)$_n$,
X (−y −y x −x)$_n$,
X (−x x −y −y)$_n$ and
X (−y −y x −x)$_n$.

As an example a NMR simulation and further processing of the first of these sequences are presented next in FIGS. 8a to 8e. A precondition is that the ringing phase really follows the pulse phase, not only if the pulse is inverted but also when the pulse phase is changed by 90°. As all the above sequences contain x, −x and y or −y pulses the echo phases first need phase rotating for the same ringing phase before we can subtract successive echoes to remove ringing. At the same time this method excludes offset removal because the offset is also rotated by say 90° and hence is no longer subtracted when we subtract two echoes. Therefore the offset must be removed either by one of the ways explained above or by a PAP of these sequences. Using a PAP we would first remove ringing for each individual sequence and remove offset afterwards by PAP. In FIGS. 8a to 8e complex (i.e. magnitude and phase) entities, like pulses, echoes or echo amplitudes are shown. The real (in-phase) part is always drawn as a solid line while the imaginary (quadrature) part is shown as a dashed or dotted line.

Figure 8A:
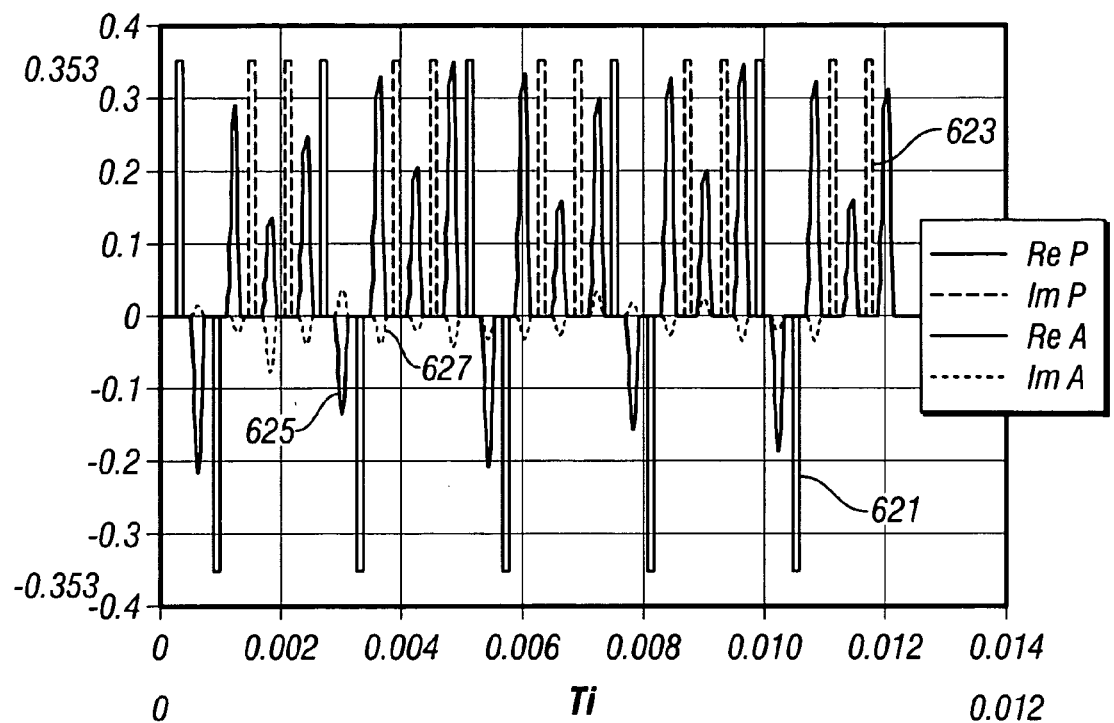
FIGS. 8a to 8e shows a simulation and further processing of the X (x −x y y)$_n$ sequence.
Figure 8B:
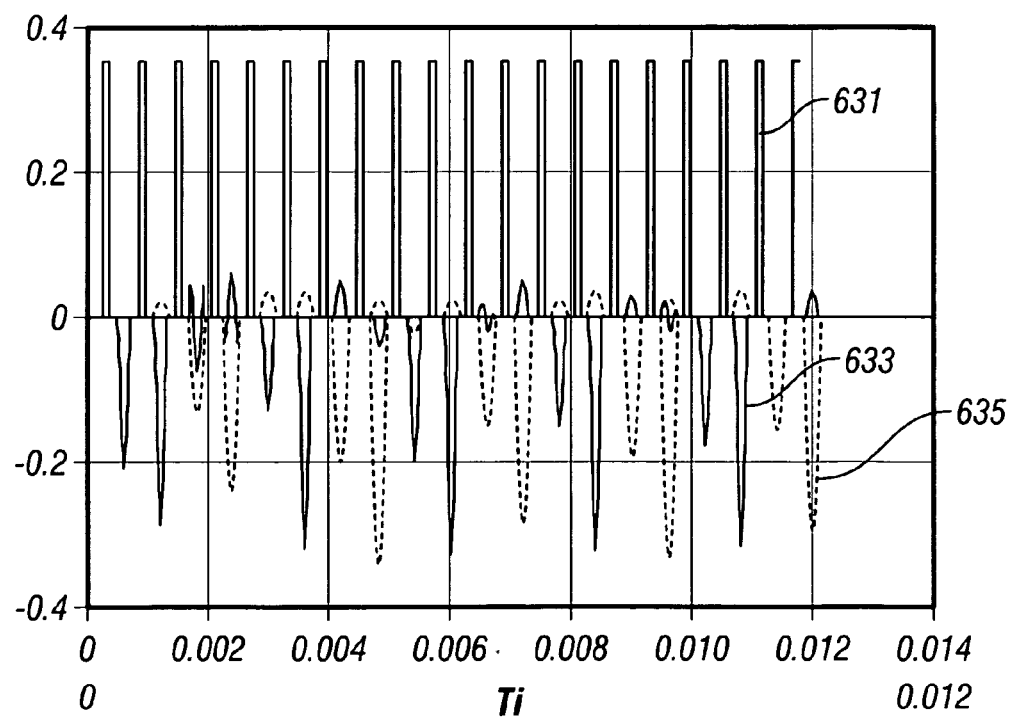

FIG. 8a shows the NMR simulation with x and −x pulses as solid rectangles 621 and y pulses 623 as dashed rectangles and the real 625 and imaginary 627 parts of the spin echo signals. The pulses 621 form pairs with alternating polarity while the pulses 623 have 90° phase shifts (and form pairs with the same relative polarity). After rotation of the individual pulses and echoes of FIG. 8a to give all ringing the same phase, the results are shown in FIG. 8b. Specifically, all echoes are rotated by a phase shift that is the inverse of the preceding pulse phase. This results in all echoes showing the same ringing. For the display, the same is done with the phase of the pulses, i.e. all pulses are now displayed with the same phase. This is a check that the phase correction has been properly applied. 631 shows the pulses while 633 and 635 show the echoes.

Figure 8C:
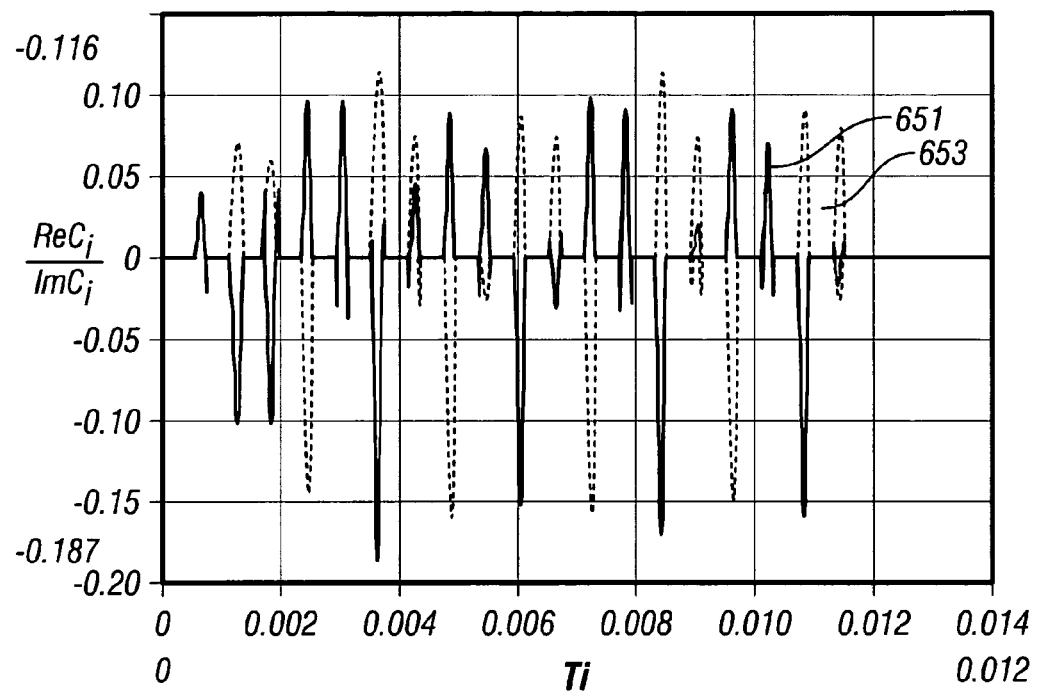
Figure 8D:
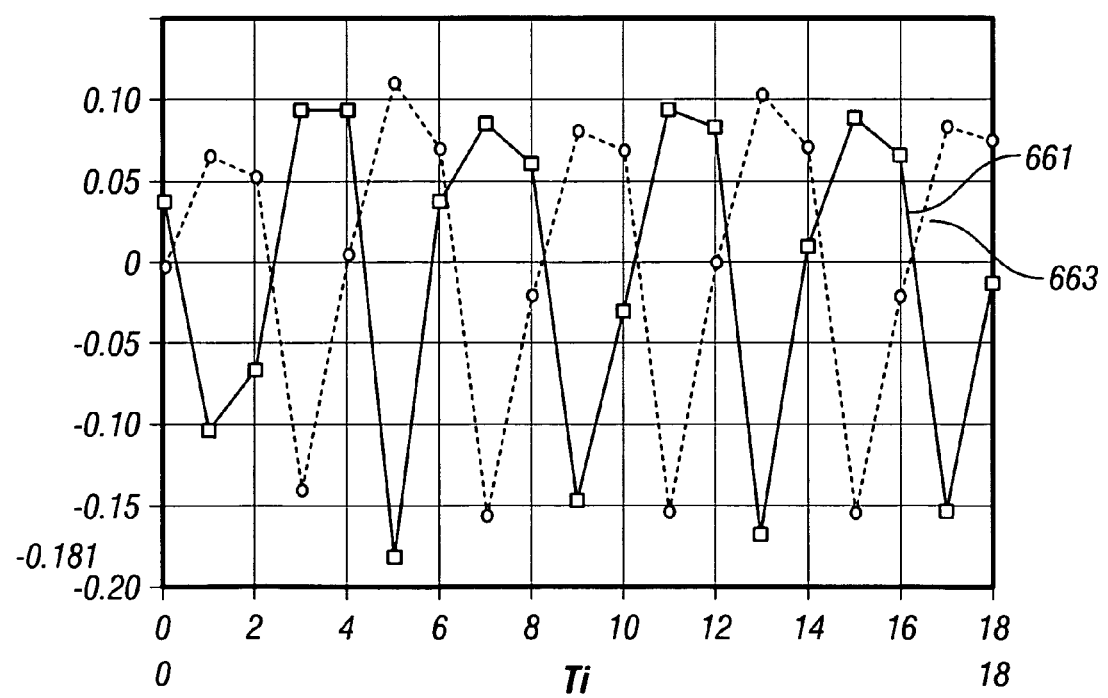

Subtraction and division by two of successive echoes of FIG. 8b gives the results of FIG. 8c where the real part is denoted by 651 and the imaginary part by 653. FIG. 8d shows the average of four points, sampled at 10 μs interval, over each echo maximum for the real 661 and imaginary 663 components. Hence each pair of points for the same n (echo counter, horizontal axis) represents a complexe effective amplitude of the n$^{th}$ echo. Individual phase correction of each echo of FIG. 8d gives the results of FIG. 8e with the real part given by 671 and the imaginary part by 673.

Figure 8E:
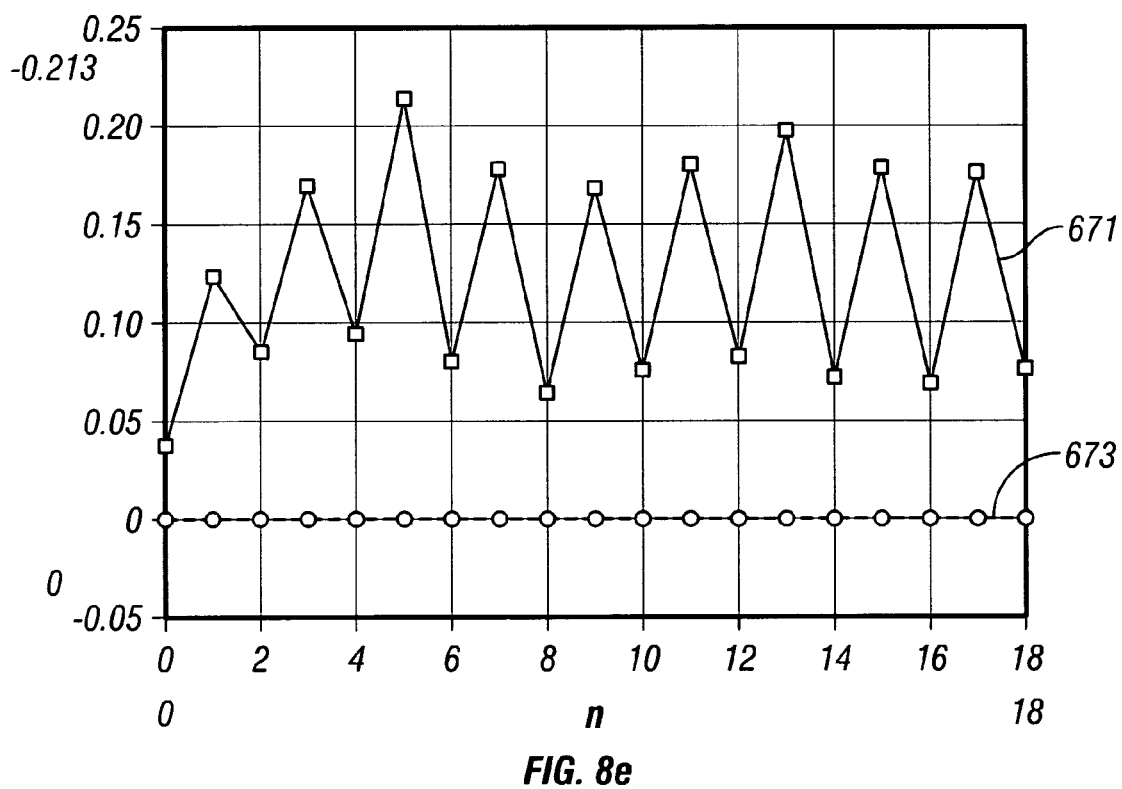

It is noted that if only every second echo of FIG. 8e is used (remember that each echo in this figure is already composed of two echoes) the amplitudes and signal-to-noise rations are about 30% less than the reference amplitudes we would get by processing the echoes of FIG. 6 or 7 in the same way, i.e. averaging 4 points over the top of each echo. However, the processing sequence shows that in principle it is possible to combine CPMG (or ORPS) and PACP, but because the signal phases do not match perfectly, we lose SNR. The processing is more complicated than that for CPMG or ORPS in that every individual echo needs individual phase rotation and stimulated echo correction. However, if non-repeatable ringing is a serious problem then this sequence may be the lesser evil. The non-repeatable ringing can arise, for example, from quartz crystals in earth formations: quartz is a major component of sandstones. In MWD measurements (where the rate of penetration is low), the ringing from quartz crystals is more likely to be repeatable than in wireline applications where the logging speed is much higher. The offset is less likely to vary with time. For this reason, with the pulse sequence of FIG. 8, the ringing should preferably be removed first and then the offset removed using a PAP.

Once the non-NMR signal (ringing or offset) has been removed, the corrected signals can then be analyzed using prior art methods to obtain properties of the earth formation. These include total porosity, effective porosity, BVI, BVM, and T$_2$ distributions.

The present invention has been discussed above with respect to measurements made by a measurement-while-drillling (MWD) assembly. This is not intended to be a limitation and, in particular, the method is equally applicable to measurements made using a wireline device or coiled tubing.

While the foregoing disclosure is directed to the specific embodiments of the invention, various modifications will be apparent to those skilled in the art. It is intended that all such variations within the scope and spirit of the appended claims be embraced by the foregoing disclosure.

The invention claimed is:

1. A method of evaluating an earth formation using a nuclear magnetic resonance (NMR) device conveyed within a borehole penetrating said formation, comprising:
   (a) producing a static magnetic field in a volume of said earth formation and aligning nuclear spins therein;
   (b) pulsing the earth formation with at least one sequence of radio frequency (RF) pulses, said at least one RF pulse sequence comprising:
      (A) an excitation pulse with a tip angle substantially equal to 90°;
      (B) a plurality of groups of refocusing pulses, each group comprising a phase-alternated pair of refocusing pulses, one pulse of said phase-alternated pair having a phase substantially equal to a phase of said excitation pulse;
   (c) obtaining a plurality of spin echo signals in response to application of said at least one pulse sequence of RF pulses; and
   (d) processing said spin echo signals to give corrected spin echo signals in which a DC offset has been reduced.

2. The method of claim 1, wherein reducing said DC offset further comprises subtracting one of said spin echo signals from an adjacent one of said spin echo signals.

3. The method of claim 1, wherein said at least one RF pulse sequence further comprises an additional RF pulse sequence including:
   (C) an excitation pulse with a tip angle substantially equal to 90°; and
   (D) a plurality of groups of refocusing pulses, each group comprising phase alternated pairs of refocusing pulses;
   wherein a phase of said excitation pulse in (C) is opposite a phase of said excitation pulse in (A) and a phase of said refocusing pulses in (D) is the same as a phase of said refocusing pulses in (B).

4. The method of claim 3 further comprising removing a ringing caused by at least one of (i) a refocusing pulse, and, (ii) crystals in said earth formation.

5. The method of claim 1 wherein at least one pulse of said pairs of refocusing pulses has a tip angle substantially equal to 180°.

6. The method of claim 1 wherein at least one pulse of said pairs of refocusing pulses has a tip angle between 90° and 180°.

7. The method of claim 1 wherein each of said plurality of groups of refocusing pulses further comprises an additional pair of refocusing pulses with a phase that is substantially one of (i) +90°, and (ii) −90°, relative to a phase of said excitation pulse.

8. The method of claim 7 wherein said additional pair of refocusing pulses precedes said phase alternated pair of refocusing pulses within one of said plurality of groups of refocusing pulses.

9. The method of claim 7 wherein said additional pair of refocusing pulses follows said phase alternated pair of refocusing pulses within one of said plurality of groups of refocusing pulses.

10. The method of claim 7 further comprising removing a ringing caused by at least one of (i) a refocusing pulse, and, (ii) crystals in said earth formation.

11. The method of claim 1 further comprising determining from said corrected spin echo signals at least one of (i) a total porosity, (ii) an effective porosity, (iii) an estimate of BVI, (iv) and estimate of BVM, and, (v) and estimate of a $T_2$ distribution.

12. A Nuclear Magnetic Resonance (NMR) apparatus conveyed in a borehole in an earth formation, the NMR apparatus comprising:
   (a) a magnet which produces a static magnetic field in said earth formation and aligns nuclear spins therein;
   (b) an antenna assembly that pulses said earth formation with at least one sequence of radio frequency (RF) pulses and receives signals resulting from said pulsing, said at least one pulse sequence including:
      (A) an excitation pulse with a tip angle substantially equal to 90°, and
      (B) a plurality of groups of refocusing pulses, each group comprising a phase-alternated pair of refocusing pulses, one pulse of said phase alternated pair having a phase substantially equal to a phase of said excitation pulse; and
   (c) a processor which analyzes said received signals and determines therefrom a corrected signal in which a DC offset has been reduced.

13. The apparatus of claim 12 wherein said received signals comprise spin echo signals.

14. The apparatus of claim 13 wherein reducing said DC offset further comprises subtracting one of said spin echo signals from an adjacent one of said spin echo signals.

15. The apparatus of claim 13 wherein at least one pulse of said pairs of refocusing pulses has a tip angle between 90° and 180°.

16. The apparatus of claim 12, wherein said at least one RF pulse sequence further comprises an additional RF pulse sequence including:
   (C) an excitation pulse with a tip angle substantially equal to 90°; and
   (D) a plurality of groups of refocusing pulses, each group comprising phase-alternated pairs of refocusing pulses;
   wherein a phase of said excitation pulse in (C) is opposite a phase of said excitation pulse in (A) and a phase of said refocusing pulses in (D) is the same as a phase of said refocusing pulses in (B).

17. The apparatus of claim 16 wherein the processor further reduces a ringing caused by at least one of (i) a refocusing pulse, and, (ii) a crystal in said earth formation.

18. The apparatus of claim 13 wherein at least one pulse of said pairs of refocusing pulses has a tip angle substantially equal to 180°.

19. The apparatus of claim 12 wherein each of said plurality of groups of refocusing pulses further comprises an additional pair of refocusing pulses with a phase that is substantially one of (i) +90°, and, (ii) −90°, relative to a phase of said excitation pulse.

20. The apparatus of claim 19 wherein said additional pair of refocusing pulses precedes said phase alternated pair of refocusing pulses within one of said plurality of groups of refocusing pulses.

21. The apparatus of claim 19 wherein said additional pair of refocusing pulses is subsequent to said phase alternated pair of refocusing pulses within one of said plurality of groups of refocusing pulses.

22. The apparatus of claim 19 wherein the processor further reduces a ringing caused by at least one of (i) a refocusing pulse, and, (ii) a crystal in said earth formation.

23. The apparatus of claim 12 wherein said processor further determines from said corrected signals at least one of (i) a total porosity, (ii) an effective porosity, (iii) an estimate of BVI, (iv) and estimate of BVM, and, (v) and estimate of a $T_2$ distribution.

24. The apparatus of claim 12 wherein said NMR apparatus is part of a bottom hole assembly used for drilling said earth formation.

25. The apparatus of claim 12 wherein said NMR apparatus is conveyed on one of (i) a wireline, and, (ii) coiled tubing, into sad borehole.

* * * * *